(12) United States Patent
Keller et al.

(10) Patent No.: US 6,585,958 B1
(45) Date of Patent: Jul. 1, 2003

(54) MEDICINAL AEROSOL FORMULATIONS

(75) Inventors: Manfred Keller, Bad Krozingen (DE); Kurt Herzog, Basel (CH); Rudi Müller-Walz, Schopfheim (DE); Holger Kraus, Rickenbach (CH)

(73) Assignee: Jago Research AG, Muttenz (CH)

( * ) Notice: Subject to any disclaimer, the term of this patent is extended or adjusted under 35 U.S.C. 154(b) by 0 days.

(21) Appl. No.: 09/744,379

(22) PCT Filed: Jul. 22, 1999

(86) PCT No.: PCT/CH99/00337

§ 371 (c)(1),
(2), (4) Date: Apr. 13, 2001

(87) PCT Pub. No.: WO00/06121

PCT Pub. Date: Feb. 10, 2000

(30) Foreign Application Priority Data

Jul. 24, 1998 (CH) ............................................. 1565/98

(51) Int. Cl.$^7$ ................................................. A61K 9/12
(52) U.S. Cl. ................ 424/45; 128/200.14; 128/200.21
(58) Field of Search ....................... 424/45; 128/200.14, 128/200.21

(56) References Cited

U.S. PATENT DOCUMENTS

| | | |
|---|---|---|
| 2,868,691 A | 1/1959 | Porush et al. |
| 3,014,844 A | 12/1961 | Thiel et al. |
| 4,139,607 A | 2/1979 | Simons et al. |
| 4,174,295 A | 11/1979 | Bargigia et al. |
| 4,397,836 A | 8/1983 | Madrange et al. |
| 4,405,598 A | 9/1983 | Brown |
| 5,225,183 A | 7/1993 | Purewal et al. |
| 5,698,630 A | 12/1997 | Andersson |
| 5,846,521 A | 12/1998 | Somani et al. |

FOREIGN PATENT DOCUMENTS

| | | |
|---|---|---|
| CA | 2075058 | 1/1991 |
| CA | 2062854 | 3/1992 |
| CA | 2086492 | 12/1992 |
| DE | 2736500 | 2/1978 |
| DE | 4003272 | 8/1991 |
| EP | 0372777 | 6/1990 |
| EP | 0504112 | 3/1992 |
| EP | 0550031 | 12/1992 |
| EP | 0885943 | 12/1998 |
| FR | 2339604 | 6/1977 |
| IE | 91350 | 8/1991 |
| JP | 61158919 | 7/1986 |
| WO | 9104011 | 4/1991 |
| WO | 9111495 | 8/1991 |
| WO | 9200061 | 1/1992 |
| WO | 9317665 | 9/1993 |
| WO | 9401511 | 1/1994 |
| WO | 9403056 | 2/1994 |
| WO | 9619198 | 6/1996 |

OTHER PUBLICATIONS

RD–17066, Aerosol propellants comprising N2O and/or CO2 (Jun. 1978) (XP 002090730).

Derwent Abstract No. AN–86–228980, Drug composition for dermatophytosis (1986) (XP 002039614).

Derwent Abstract No. AN–89–184245, Aerosol pressure packs for administration for medicaments (1989) (XP 002039615).

Primary Examiner—Michael G. Hartley
Assistant Examiner—M. Haghighatian
(74) Attorney, Agent, or Firm—Selitto, Behr & Kim

(57) ABSTRACT

A pressure-liquefied propellant mixture for aerosols, comprising dinitrogen monoxide and a hydrofluoroalkane having 1 to 3 carbon atoms, in particular 1,1,1,2-tetrafluoroethane and/or 1,1,1,2,3,3,3-heptafluoropropane, makes possible an improvement in the wetting properties of pharmaceutically active compounds, whereby the formulation problems existing with hydrofluoroalkanes can be overcome with respect to suspension and solution aerosols and thus improved medicinal aerosol formulations can be obtained. With the aid of dinitrogen monoxide, it is also possible to influence the pressure and thus the particle size distribution specifically and, by displacement of oxygen from the hydrofluoroalkanes, to improve the storage stability of oxidation-sensitive active compounds. If desired, the propellant mixture can additionally contain carbon dioxide.

51 Claims, No Drawings

MEDICINAL AEROSOL FORMULATIONS

This application is a 371 of PCT/CH/99/00337, filed Jul. 22, 1999.

FIELD OF THE INVENTION

The present invention relates to a pressure-liquefied propellant mixture based on hydrofluoro-alkanes, the use of this propellant mixture in aerosol formulations, and a process for the preparation of the aerosol formulations.

BACKGROUND OF THE INVENTION

Many gases, such as carbon dioxide and nitrogen, can indeed be liquefied under pressure, but are not suitable as propellants for metered-dose aerosols, because the internal pressure in the container decreases very greatly as it becomes more empty. For this reason, only those propellants are used for medicinal metered-dose aerosols, which propellants can be liquefied at room temperature and in any case only lead to a slight decrease in the internal pressure in the container when the contents are successively removed by spraying. These include the short-chain alkanes, such as propane, butane and isobutane, and the chlorofluorocarbons (CFCs), such as trichlorofluoromethane (F11), dichlorodifluoromethane (F12) and 1,2-dichloro-1,1,2,2-tetrafluoroethane (F114).

WO-A-93/17665 in fact discloses a method for the administration of physiologically active compounds, in which a supercritical liquid solution is formed from a supercritical liquid solvent and the active compound and this is then converted into the subcritical range. The supercritical solvent used was carbon dioxide, it being stated that, in addition to carbon dioxide, dinitrogen oxide, chlorofluorocarbons such as dichlorodifluoromethane and trichlorofluoromethane, xenon, sulfur hexafluoride, ethanol, acetone, propane, water and mixtures thereof are suitable.

In Research Disclosure (1978), 170, 58, XP-002090730, it was further mentioned that some fluorocarbon and chlorofluorocarbon propellants can be used in aerosol products such as hairsprays, deodorants and antiperspirants as co-propellants together with carbon dioxide or dinitrogen monoxide. The 2,2-dichloro-1,1,1-trifluoroethane (F123), 1,2-dichloro-1,1-difluoroethane (F132b), 2-chloro-1,1,1-trifluoroethane (F133a), 1,1-dichloro-1-fluoroethane (F114b) and 1-chloro-1,1-difluoroethane (F142b) mentioned as examples are chlorinated and, moreover, not very customary propellants. A hairspray in which trifluoromonochloroethane (F133a) together with carbon dioxide and/or dinitrogen monoxide is used as a propellant mixture is also disclosed in U.S. Pat. No. 4,397,836.

On account of the ozone problem caused by the elimination of free-radical chlorine atoms from CFCs, in the Montreal Agreement many countries came to an understanding that they would no longer use CFCs as propellants in future. Suitable CFC substitutes for the medicinal field are fluorinated alkanes (in the context of the present invention also designated as HFA), especially 1,1,1,2-tetrafluoroethane (HFA 134a) and 1,1,1,2,3,3,3-heptafluoropropane (HFA 227), as these are inert and have a very low toxicity. On account of their physical properties, such as pressure, density, etc., they are particularly suitable for replacing CFCs such as F11, F12 and F114 as propellants in metered-dose aerosols.

U.S. Pat. No. 4 139 607, on the other hand, proposed a propellant system formed from liquefied bis(difluoromethyl) ether and gaseous carbon dioxide, which in contrast to combinations of carbon dioxide with other known propellants such as trichloro-fluoromethane or methylene chloride should afford satisfactory aerosol samples, but, however, has not been accomplished. The document in fact mentions that other propellants such as dinitrogen monoxide, hydrocarbons and fluorohydrocarbons or liquid carriers, such as ethanol, perchloroethylene, trichloroethylene, acetone, amyl acetate, water and the like, can be added to the propellant system; the disclosed formulations, however, mostly contain about 50% of ethanol. In Derwent Abstract AN 89-184245, it is only stated that in aerosol pressure packs for the administration of medicaments instead of CFCs, hydrocarbons, such as butane and pentane, other compressed gases, such as carbon dioxide, dimethyl ether, nitrogen and dinitrogen oxide, or fluorohydrocarbons could also be used.

Medicinal aerosol preparations containing hydrofluoroalkanes such as HFA 134a are already embraced by the teaching of U.S. Pat. No. 2,868,691 and U.S. Pat. No. 3,014,844 and disclosed in DE-A-2 736 500 and EP-A-0 372 777. Examples of formulations containing HFA 227 are found, for example, in WO-A-91/11495, EP-A-0 504 112 and EP-B-0 550 031. It is known from various publications that the customary excipients used in CFC-containing metered-dose aerosols, such as lecithin, sorbitan trioleate and oleic acid, only dissolve inadequately in hydrofluoroalkanes such as HFA 134a and HFA 227, because a chain extension and the substitution of the chlorine atoms by fluorine atoms leads to a worsening of the solubility properties of the permitted excipients mentioned. Even in the case of CFCs, which are considerably better solvents than HFAs, ethanol or other cosolvents were often added to improve the solubility in order to be able to administer pharmaceutical substances such as isoprenaline and epinephrine (cf. U.S. Pat. No. 2,868,691) as an aerosol. It was therefore obvious to improve not only the solubility of CFCs, but also that of HFAs, by addition of ethanol. Examples of this are found in the technical literature and in various patent applications. Alternatively to this, there are a number of developments of pressure-liquefied aerosol preparations containing HFA 134a and/or HFA 227 which use propellant-soluble excipients, such as fluorinated surface-active substances (WO-A-91/04011), mono- or diacetylated glycerides (EP-A-0 504 112) or polyethoxylated compounds (WO-A-92/00061), which can be dissolved in the necessary amount in the two propellants even without addition of ethanol.

For CFC-free medicinal aerosol preparations having a high vapor pressure, the propellant preferably used today is usually HFA 134a (vapor pressure about 6 bar at 20° C.) and for those with a lower vapor pressure it is HFA 227 (vapor pressure about 4.2 bar at 20° C.). Both propellants differ with respect to their density (about 1.4 mg/ml for HFA 227 and about 1.2 mg/ml for HFA 134a at 20° C.), which is particularly of importance for suspensions. If the active compound has a higher density than the propellant, sedimentation occurs; if its density is lower, flotation occurs. To solve the problem, it is therefore suggested under certain circumstances to use propellant mixtures and/or, to lower the density, to add cosolvents such as ethanol, diethyl ether or other low-boiling solvents or propellants such as n-butane. A significant disadvantage of the hydrofluoroalkanes is their relatively low dissolving power in comparison with CFCs, in particular in comparison with F11. The solvent properties decrease with increasing chain length in the sequence F11>HFA 134a >HFA 227. For this reason, the suspending aids customarily used in CFCs, such as sorbitan trioleate, lecithin and oleic acid, can no longer be dissolved in the customary concentrations (weight ratios of typically approximately 1:2 to 1:20, based on the active compound) by addition of polar solvents without increasing the hydrophilicity.

It is generally known that in the case of suspension formulations only active compound particles which are smaller than 6 $\mu$m are respirable. For the desired deposition thereof in the lungs, these must therefore be comminuted or micronized before processing by means of special procedures, such as using pinned-disk, ball or air-jet mills. A grinding process as a rule leads to an increase in surface area, which is accompanied by an increase in the electrostatic charge of the micronized active compound, on account of which the flow behaviour and the active compound dispersion is usually impaired. As a result of the interfacial and charge activities, there is often an agglomeration of active compound particles or alternatively adsorption of active compound at interfaces, which becomes conspicuous, for example, in the accumulation on equipment or container surfaces.

In aerosol preparations in which the active compound is present suspended in liquefied propellant, adsorption or ring formation in the container can occur at the place where the liquid phase changes into the gas phase. Without wetting the micronized active compound particles or conducting away charges and modifying their surface properties, problems can occur during dispersion or suspension, in the hydrofluoroalkanes mentioned. The lack of wetting or dispersion of the active compound particles also results in these in many cases having a high adsorption tendency and adhering to surfaces, such as the container inner wall or the valve, which then leads to an underdosage and to a poor dosage accuracy from puff of spray to puff of spray. In the case of suspensions, it is therefore necessary as a rule to add a surface-active substance or a glidant in order to lower the adsorption at interfaces, to stabilize the suspensions and to ensure the dosage accuracy. A change or reduction in the proportion of the inhalable, respirable particles, the so-called fine particle fraction (FPF) or fine particle dose (FPD), occurring in the course of storage, which leads to a decrease in the activity of the HFA preparation, is particularly problematical.

To overcome the problems presented above, as a rule surface-active substances are therefore added, as were already used earlier in the CFC-containing formulations. Alternatively to this, in certain cases a modification of the surface properties by means of various measures (e.g. coating) may help to minimize these undesired effects. Because, however, surface-active agents such as oleic acid, sorbitan trioleate and lecithin only dissolve inadequately in hydrofluoroalkanes such as HFA 134a and HFA 227, in many cases ethanol is or must be added as a cosolvent so that the pharmaceutical technology problems can be controlled better.

If, however, ethanol is added in a higher concentration, the density of the propellant mixture is reduced, which can lead to an undesired sedimentation of active compound, especially in the case of suspensions. Moreover, a "wet spray" can undesirably be obtained, because the propellant evaporates much more rapidly than ethanol. In addition, however, as a result of the increase in solubility during storage, the active compounds can also start to dissolve, which then leads to crystal growth and thus, in turn, to a reduction in the amount of inhalable, respirable particles, the so-called fine particle dose (FPD).

To measure the aerodynamic particle size distribution or the proportion of the dose which can be deposited in the lungs, the so-called fine particle dose (FPD), of inhalable, respirable particles in an aerosol, impactors, such as the 5-stage multistage liquid impinger (MSLI) or the 8-stage Andersen cascade impactor (ACI), which are described in Chapter <601> of the United States Pharmacopeia (USP) or in the Inhalants Monograph of the European Pharmacopeia (Ph. Eur.) are suitable. Using these apparatuses, the aerodynamic deposition behaviour of the aerosol cloud can be investigated in the laboratory (in vitro). By means of a "log-probability plot" (logarithmic representation of the probability distribution), the mean aerodynamic particle diameter (Mass Median Aerodynamic Diameter (MMAD)) of aerosol preparations can then be calculated. From this, it can be deduced whether the active compound is more likely to be deposited in the upper or lower area of the lungs.

If the active compound is present in the HFA propellant/ethanol mixture not in suspended form, but in dissolved form, problems with respect to the standard deviation of the dosage accuracy per stroke are usually less pronounced. If, however, a larger amount of ethanol is used for this, on rinsing empty the container a "head space" effect occurs as follows: the proportion of ethanol, which has a lower vapor pressure and a lower density, increases and that of propellant having higher density and higher vapor pressure decreases. On spraying or as the container becomes more empty, the concentration ratio of propellant to ethanol changes, which on account of the density difference leads to a reduction in the mass of a puff of spray and thus also in the content of a puff of spray or active compound. It is additionally disadvantageous that at higher ethanol concentrations of, for example, 10%–30%, the content of inhalable particles (<6 $\mu$m) usually decreases, because the spray affords droplets having a greater aerodynamic diameter on account of the different evaporation properties of ethanol in comparison to the propellant. As a result of this, there is a reduction in the fine particle dose (FPD) which is crucial for the activity.

In a solution aerosol with the same ethanol content, a higher fine particle fraction (FPF), i.e. a greater percentage of inhalable droplets, is customarily obtained with HFA 134a in comparison to HFA 227, which is to be attributed to the higher pressure of HFA 134a. In principle, it is true that the higher the internal pressure in the aerosol container, the finer the particle spectrum of the aerosol cloud. Solution aerosols having a low ethanol content therefore as a rule have a smaller MMAD (0.8–1.5 $\mu$m) than suspension aerosols (2–4 $\mu$m), when using fine atomizing nozzles. This is connected with the fact that droplets are generated as an aerosol cloud in the case of solution aerosols and particles in the case of suspension aerosols.

For the topical application of active compounds in the area of the bronchi and bronchioles, particle sizes of about 2–4 $\mu$m are advantageous, as are customarily achieved with suspension formulations. Smaller particles which pass into the alveolar area are partly exhaled (<0.5 $\mu$m) or pass into the systemic circulation by absorption. It follows from this that aerosol preparations for systemic application should favourably have particle sizes of about 0.5 $\mu$m–2 $\mu$m, where, for example, a monodisperse aerosol having a very high proportion of particles in the range of about 1 $\mu$m would be particularly advantageous. Depending on the desired site of deposition, a smaller or larger MMAD and, if appropriate, a monodisperse distribution spectrum are therefore preferred. The following holds with respect to the aerodynamics: the greater the mass of the particles the greater their tendency to fly on in a straight line. It results from this that if there is a change in the direction of flow, impaction of particles occurs. It is known from deposition studies that even in the case of an optimum inhalation maneuver only about 20% of the particles emitted from a metered-dose aerosol pass into the lungs and almost 80% impact in the oropharynx.

In the case of ethanol-containing solution aerosols, unfortunately there are frequently problems concerning the active compound stability. Active compounds, such as fenoterol and salbutamol are affected by this, which is why such active compounds have preferably been formulated as suspensions until now. To reduce their solubility in the propellant mixture, the polar salts such as fenoterol hydrobromide are also frequently employed.

SUMMARY OF THE INVENTION

The invention is therefore based on the object of making available a propellant system with which:
- active compounds can be better wetted;
- suspension aerosols having improved suspension and shelf-life properties can be prepared;
- solution aerosols having improved storage stability and lower addition of ethanol can be prepared;
- the dosage accuracy can be improved;
- the particle size distribution spectrum and the MMAD can be better adjusted; and/or
- the fine particle dose (FPD) can be increased and the oropharyngeal deposition can be reduced.

This object is achieved according to the invention by a pressure-liquefied propellant mixture for aerosols, comprising dinitrogen monoxide and a hydrofluoroalkane of the general formula $$C_xH_yF_z \qquad (I)$$

in which x is the number 1, 2 or 3, y and z are each an integer ≧1 and y+z=2x+2.

DETAILED DESCRIPTION OF THE INVENTION

Surprisingly, it was in fact found that the targets mentioned are achieved and propellant mixtures having more advantageous properties can be obtained if a small amount of dinitrogen monoxide (laughing gas) is added to propellants based on hydrofluoroalkanes. If desired, a small amount of carbon dioxide, which brings about similar improvements, can additionally be added to the propellant. Gas mixtures of this type—in contrast to dinitrogen oxide or carbon dioxide as the sole propellant—show only a slight decrease in the internal pressure in the container as it becomes more empty, which makes possible their use as propellants for metered-dose aerosols. As is illustrated in Table 1 with the aid of some examples, propellant mixtures of this type can be employed in a wide temperature range for metered-dose aerosols. This effect is also observed if the propellant mixture or the aerosol formulation additionally contains a cosolvent such as ethanol.

TABLE 1

Temperature dependence of $N_2O$-containing hydrofluoroalkanes with or without ethanol (EtOH) as cosolvent

| Parts by weight | | | | Pressure (bar) at | | | | |
|---|---|---|---|---|---|---|---|---|
| HFA 227 | HFA 134a | $N_2O$ | EtOH | 4° C. | 20° C. | 30° C. | 40° C. | 50° C. |
| 600 | 0 | 2 | 0 | 2.00 | 3.75 | 5.25 | 7.25 | 9.50 |
| 600 | 0 | 6 | 0 | 2.25 | 4.50 | 6.00 | 8.25 | 10.50 |
| 555 | 0 | 2 | 45 | 1.50 | 3.25 | 4.75 | 6.75 | 8.25 |
| 555 | 0 | 6 | 45 | 2.00 | 4.00 | 5.50 | 7.25 | 9.25 |
| 420 | 0 | 2 | 180 | 1.00 | 2.50 | 3.75 | 5.00 | 6.50 |
| 420 | 0 | 6 | 180 | 1.75 | 3.25 | 4.50 | 6.00 | 7.50 |
| 420 | 0 | 12 | 180 | 2.75 | 4.50 | 6.00 | 7.50 | 9.25 |
| 0 | 600 | 2 | 0 | 2.50 | 5.50 | 7.50 | 10.00 | 12.50 |
| 0 | 600 | 6 | 0 | 3.00 | 6.00 | 8.00 | 10.50 | 13.75 |
| 240 | 360 | 2 | 0 | 2.50 | 5.00 | 7.00 | 9.25 | 12.00 |
| 240 | 360 | 6 | 0 | 3.00 | 5.50 | 7.50 | 10.00 | 13.00 |
| 0 | 420 | 2 | 180 | 2.50 | 4.50 | 6.00 | 8.00 | 10.25 |
| 0 | 420 | 6 | 180 | 3.00 | 5.25 | 6.75 | 8.75 | 11.00 |

Surprisingly, it has further been found that by the addition of dinitrogen oxide and, if desired, carbon dioxide to hydrofluoroalkanes such as HFA 134a and/or HFA 227 the suspension of pharmaceutical active compounds is facilitated and the tendency to adhesion and adsorption of active compounds on interfaces is deceased. Using propellant mixtures of this type, suspensions which are distinguished by controlled flocculation can therefore be prepared more easily, and as a result of the better suspension properties, in many cases the addition of—in some cases undesired—surface-active suspension aids and/or cosolvents can be dispensed with or at least their proportion can be deceased. By addition of glidants such as glycerol or polyethylene glycol, suspension or solution aerosols having improved properties can often be obtained.

In addition, it has been found that the undesired deposition of active compound in the oropharynx can be reduced and at the same time the FPD can be increased.

With the aid of dinitrogen oxide and, if desired, carbon dioxide, it is also possible to displace oxygen from the hydrofluoroalkanes, as a result of which the storage stability of oxidation-sensitive active compounds is improved. Moreover, by addition of dinitrogen oxide and, if desired, carbon dioxide, the internal pressure in the aerosol container can be adjusted such that in comparison to a conventional CFC or HFA metered-dose aerosol the FPF and MMAD can be virtually aligned as appears most sensible for the respective application. It is thus possible to produce MDIs (Metered-dose Inhalers) for both topical application and systemic administration. In particular for systemic administration, completely new possibilities of use are opened up, because virtually monodisperse aerosols having high respirable fractions can be produced in combination with suitable atomizing nozzles.

The propellant mixture according to the invention thus also offers advantages in the case of suspension and solution aerosol formulations, in which a surface-active agent and/or a cosolvent is necessary or desired. On the one hand, the use of propellants which contain dinitrogen oxide and, if desired, carbon dioxide frequently permits a reduction in the amount of cosolvent needed and a better solubility of conventional surface-active agents. On the other hand, the disadvantageous influence of cosolvents such as ethanol on the droplet size can be avoided completely or to the greatest possible extent, since as a result of a corresponding increase in the concentration of dinitrogen oxide and, if desired, carbon dioxide even at comparatively high cosolvent concentrations, the internal pressure and the deposition behaviour can be adjusted such that both the fine particle dose and the MMAD can be adjusted in a therapy-compliant manner.

The preparation of the propellant mixtures according to the invention can be carried out in a manner known per se by introducing dinitrogen monoxide and, if desired, carbon dioxide, under pressure into a hydrofluoroalkane of the formula I.

The propellant mixture according to the invention is suitable in principle for any desired aerosol applications such as cosmetic and household sprays. On account of the advantages described—such as the small fall in the internal pressure on emptying, lower temperature dependence and easier adjustability of the internal pressure, improved wetting properties for pharmaceutical active compounds and usability of conventional surface-active agents such as oleic acid, lecithin and sorbitan trioleate—the propellant mixture according to the invention, however, is especially also suitable for medicinal aerosol formulations and in particular for inhalation aerosols.

The invention therefore likewise relates to a medicinal aerosol formulation, comprising an efficacious amount of a pharmaceutically active compound, and a pressure-liquefied propellant mixture, containing dinitrogen monoxide and a hydrofluoroalkane of the general formula $$C_xH_yF_z \qquad (I)$$

in which x is the number 1, 2 or 3, y and z are each an integer ≧1 and y+z=2x+2.

Examples of suitable hydrofluoroalkanes which can be used in the propellant mixtures and aerosol formulations according to the invention are: difluoromethane (HFA 32), pentafluoroethane (HFA 125), 1,1,2,2,-tetrafluoroethane (HFA 134), 1,1,1,2-tetra-fluoroethane (HFA 134a), 1,1,2-trifluoroethane (HFA 143), 1,1,1-trifluoroethane (HFA 143a), 1,1-difluoro-ethane (HFA 152a), 1,1,1,2,3,3,3-heptafluoropropane (HFA 227), hexafluoropropane (HFA 236), pentafluoro-propane (HFA 245) and the like. In general, hydrofluoroalkanes having 2 or 3 hydrocarbons are preferred. Particularly preferred propellant mixtures and aerosol formulations are those which contain 1,1,1,2-tetrafluoroethane (HFA 134a), 1,1,1,2,3,3,3-heptafluoropropane (HFA 227) or a mixture of the two, for example a 1:1 mixture.

The propellant mixtures and aerosol formulations according to the invention preferably contain at least approximately 0.0001% by weight, in particular at least approximately 0.01% by weight, of dinitrogen monoxide. If desired, the propellant mixtures and aerosol formulations can additionally contain a small amount of carbon dioxide. The content of dinitrogen monoxide and carbon dioxide is dependent, inter alia, on the pressure desired, the nature of the hydrofluoroalkanes used and the nature and amount of possible further propellants and cosolvents and the like. In general, however, the content of dinitrogen monoxide or the content of dinitrogen monoxide and carbon dioxide together is approximately 0.0001 to 10% by weight, preferably approximately 0.01 to 6% by weight and particularly preferably approximately 0.1 to 3% by weight. In the case of medicinal aerosols and in particular in inhalation aerosols, in general a content of dinitrogen monoxide or of dinitrogen monoxide and carbon dioxide together of approximately 0.01 to 2% by weight, typically approximately 0.1 to 1.0% by weight, is preferred; as a rule higher concentrations are only indicated if the formulation contains a comparatively high content of cosolvents such as ethanol or water.

The expression "pharmaceutically active compound" in the context of the present invention comprises therapeutically active compounds and vaccines and other substances for health prophylaxis. Suitable pharmaceutically active compounds for the aerosol formulations according to the invention are basically all active compounds which can be administered as an aerosol, such as beta-mimetics, corticosteroids, anticholinergics, cyclooxygenase, mast cell, lipoxygenase and proteolytic enzyme inhibitors, arachidonic acid, leukotriene, thromboxane, sodium/potassium channel, neurokinin, tachykinin, bradykinin, muscarine, histamine, phosphodiesterase, platelet-activating factor and selectin antagonists, potassium channel blockers, antiinfectives, antibiotics, pentamidine, cytostatics, fungistatics, free-radical scavengers, vitamins, hormones, immunostimulants, immunosuppressants, mucolytics, heparin, antidiabetics, analgesics, soporifics and the like, for example:

beta-mimetics such as salbutamol, formoterol, salmeterol, fenoterol, clenbuterol, terbutaline, bambuterol, broxaterol, epinephrine, isoprenaline, orciprenaline, hexoprenaline, tolbuterol, reproterol, bamethan, tetroquinol, levalbuterol etc., corticoids such as beclomethasone, dexamethasone, ciclomethasone, triamcinolone, budesonide, butixocort, ciclesonide, fluticasone, flunisolide, icomethasone, mometasone etc., anticholinergics and spasmolytics such as atropine, glycopyrronium bromide, scopolamine, N-butylscopolamine, trospium chloride, ipratropium bromide, oxitropium bromide, tiotropium bromide, droferine, oxybutinin, moxaverine etc., mast cell and histamine inhibitors such as cromoglycic acid, nedocromil, pemirolast etc., and 5-lipoxygenase inhibitors such as zileuton, linazolast etc., leukotriene antagonists such as iralukast, zafirlukast, montelukast, roflumilast, imitrodast, ontozolast and pranlukast, sodium channel antagonists such as amiloride, potassium channel antagonists such as bimakalim, arachidonic acid antagonists such as 2-benzoxazolamine, histamine receptor antagonists such as epinastine, cetrizine, mizolastine and mequitamium, anti-migraine agents such as ergot alkaloids, methysergide, ergotamine, serotonin, sumatriptan, zolmitriptan, cyclandelate etc., analgesics such as fentanyl, morphine, buprenorphine, opium, heroin, nalbuphine, pentazocine, oxycodone, tramadol, pethidine, tilidine, methadone, nefopam, dextropropoxyphene, piritramide etc., mucolytics such as RNase, acetylcysteine, ambroxol, apafant, bromhexine, human lung surfactant etc., antiemetics such as bromopride, domperidone, metoclopramide, triethylperazine, trifluoropromazine, meclozine, chlorophenoxamine, dimenhydrinate etc., antibiotics such as penicillins (e.g. azocillin), cephalosporins (e.g. cefotiam or ceftriaxone), carbapenems, monobutams, aminoglycosides (e.g. streptomycin, neomycin, gentamycin, amikacin or tobramycin), quinolones (e.g. ciprofloxacin), macrolides (e.g. erythromycin), nitroimidazoles (e.g. tinidazole), lincosamides (e.g. clindamycin), glycopeptides (e.g. vancomycin), polypeptides (e.g. bacitracin) etc., vitamins and free-radical scavengers such as vitamin A, B, C, D or E, catalase, superoxide dismutase, reduced glutathione etc., antidiabetics such as glibenclamide, glipizide, gliclacide, glimepiride, troglitazone etc., soporifics such as benzodiazepines, piperidinediones, antihistamines etc., neuroleptics, antidepressants and anticonvulsants such as benzodiazepines, phenothiazines, butyrophenones, sulpiride, hydantoins, barbiturates, succinimides, carbamazepine etc., hormones such as androgens (e.g. testosterone), antioestrogens, oestrogens (e.g. estradiol), gestagens (e.g. progesterone), corticosteroids, calcitonin, parathyrin, somatotropin, oxytocin, prolactin, glucagon, erythropoietin, atriopeptin, melanotropin, thyrotopin, gonadotropin, vasopressin, insulin etc., potency agents such as phentolamine, sildenafil, alprostadil etc., cytostatics such as nitrogen mustard derivatives (e.g. ifosphamide), N-nitrosourea derivatives (e.g lomustine), antagonists of purine and pyrimidine bases (e.g fluorouracil), platinum complexes (e.g. carboplatin), anthracyclines (e.g. doxorubicin), podophylline derivatives (podophyllotoxin).

The active compounds mentioned can optionally be used in the form of their isomers, enantiomers or racemates and, in the case of acids or bases, as such or in the form of their pharmaceutically acceptable salts or derivatives. The optimum amount of active compound in the formulations according to the invention depends on the particular active compound. As a rule, however, aerosol formulations are preferred which contain at least approximately 0.0001 and at most approximately 5% by weight, in particular approximately 0.01 to 3% by weight, of active compound.

Examples of active compounds which can be preferably used are the antiasthmatics such as beta-mimetics, corticosteroids and anticholinergics and antiallergics such as mast cell inhibitors. Aerosol formulations which contain salbutamol, formoterol, salmeterol, fluticasone, budesonide, ciclesonide, glycopyrronium, tiotropium, cromoglycic acid, nedocromil, mometasone, sildenafil, beclomethasone, levalbuterol or a pharmaceutically acceptable salt or derivative of these active compounds are particularly preferred.

Depending on the nature of the active compounds and further additives, the aerosol formulations according to the invention can be present in the form of suspensions, emulsions or solutions. The aerosol formulations can be prepared in a manner known per se by introducing dinitrogen monoxide under pressure into a liquefied hydrofluoroalkane of the formula I and adding the pharmaceutically active compound. The dinitrogen monoxide and the active compound can basically be added in any desired sequence. In the case of suspension formulations, however, as a rule it is preferred firstly to introduce the dinitrogen monoxide into the propellant and then to add the micronized active compound. The micronization of the active compound can take place in a known manner and is preferably carried out such that a particle size of approximately 0.5 to 6 $\mu$m is obtained. If carbon dioxide is additionally added to the aerosol formulation, this can be introduced under pressure to the liquefied hydrofluoroalkane either separately or together with the dinitrogen monoxide.

The propellant mixtures and aerosol formulations according to the invention can contain one or more hydrofluoroalkanes and, if desired, further propellants. Preferably, however, they contain no chlorofluorocarbons. Particularly preferred propellant mixtures and aerosol formulations are in general those which—apart from compounds such as water, lower alkanes, lower alcohols and lower ethers which can be used, if desired, as cosolvents—contain as propellants only dinitrogen monoxide and one or more hydrofluoroalkanes of the formula I and, if desired carbon dioxide. The hydrofluoroalkane or the hydrofluoroalkanes and the carbon dioxide concentration are preferably selected such that an internal pressure of approximately 3 to 10 bar, particularly preferably approximately 3.5 to 6 bar, can be established at 20° C. in the aerosol container.

The aerosol formulations according to the invention are suitable for suspension, emulsion and solution formulations, and they can contain customary additives such as cosolvents, glidants or lubricants (e.g. glycerol) and surface-active agents. The addition of the active compound and possible further additives can be carried out in a manner known per se. As a result of the improvement of the fine particle fraction achievable according to the invention and the simultaneous reduction in the undesired oropharyngeal deposition, it is frequently possible to decrease the active compound concentration significantly in comparison to a CFC-containing metered-dose aerosol.

The use of a cosolvent is frequently indicated, in particular in solution formulations, but can occasionally also be advantageous in suspension formulations.

Suitable cosolvents are in particular water, lower alcohols, lower alkanes and lower ethers, preferably water, alcohols having 1 to 3 carbon atoms, alkanes having 3 to 6 carbon atoms and dialkyl ethers having 2 to 4 carbon atoms, such as water, ethanol, propanol, isopropanol, ethylene glycol, propylene glycol, glycerol, propane, butane, isobutane, pentane, dimethyl ether, diethyl ether and the like. Diethyl ether and in particular ethanol are particularly preferred. The proportion of cosolvent in the propellant mixtures and aerosol formulations according to the invention, if present, can in general be approximately 0.01 to 40% by weight, in particular approximately 0.1 to 15% by weight, based on the total mixture or the total formulation.

The proportion of one or more hydrofluoroalkanes of the formula I in the propellant mixtures and aerosol formulations according to the invention is in general at least approximately 40% by weight, preferably at least approximately 64% by weight and particularly preferably at least approximately 87% by weight, of the total mixture or of the total formulation. In the case of the medicinal aerosol formulations, however, the proportion of hydrofluoroalkanes with respect to the content of active compound, surface-active agent and possible further additives can also be lower and can be, for example, at least approximately 30% by weight.

The use of a surface-active agent is frequently indicated, in particular in the case of suspension formulations, but can also be advantageous in solution formulations, e.g. for valve lubrication. In principle all customary surface-active agents are suitable, such as oleic acid, lecithin, sorbitan trioleate, cetylpyridinium chloride, benzalkonium chloride, polyoxyethylene (20) sorbitan monolaurate, polyoxyethylene (10) stearyl ether, polyoxyethylene (2) oleyl ether, polyoxyethylene (20) sorbitan monostearate, polyoxyethylene (20) sorbitan monooleate, polyoxypropylene/polyoxyethylene block copolymers, polyoxypropylene/polyoxyethylene/ethylenediamine block copolymers, ethoxylated castor oil and the like. In general, oleic acid, sorbitan trioleate and lecithin are preferred. The proportion of surface-active agent, if present, can preferably be approximately 0.0001 to 1% by weight, in particular approximately 0.001 to 0.1% by weight, based on the total formulation. Preferably, however, the aerosol formulations according to the invention can also be essentially free of surface-active agents, i.e. can contain less than 0.0001% by weight of surface-active agents.

Furthermore, the aerosol formulations according to the invention can contain, if desired, buffer substances or stabilizers such as citric acid, ascorbic acid, sodium EDTA, vitamin E, N-acetylcysteine and the like. In general, such substances, if present, are used in amounts of not more than approximately 1% by weight, for example approximately 0.0001 to 1% by weight, based on the total formulation.

The aerosol formulations according to the invention can be prepared in a manner known per se using stirrers and homogenizers. For filling, known processes, such as the cold- or pressure-filling technique or modifications of these techniques, can be employed. Suitable containers are, for example, pressure-resistant containers made of glass, plastic or aluminum, which can be equipped with metered-dose valves of, for example 10 to 140 $\mu$l and can be provided with commercially available—also inspiration-triggered—mouth tube adapters.

In the preparation of aerosol formulations, the propellant mixtures according to the invention thus offer a number of advantages, such as better wetting of active compound, improved suspension and shelf-life properties of suspension formulations, improvement in the dosage accuracy, increase in the fine particle dose and, if desired, a decrease in the amounts of cosolvent or the wide avoidance of the disadvantages of high amounts of cosolvent.

The invention therefore likewise relates to the use of the propellant mixtures according to the invention as propellants for aerosols, the use for medicinal aerosols and in particular for nasal or inhalant aerosols (which can preferably have an aerodynamic particle or droplet diameter of approximately 0.5 to 40 $\mu$m, in particular approximately 0.5 to 6 $\mu$m) being preferred, and the use in a pressure-resistant container having a metered-dose valve and a suitable adapter for the atomization or inhalation of pharmaceutical active compounds.

Using the propellant system according to the invention, it is possible to prepare, for example, a budesonide metered-dose aerosol which, in comparison to a CFC-containing commercial product (Pulmicort®, Astra, Sweden) has a far better dosage accuracy and an FPF which is almost twice as high. Supplementary to this, the deposition in the mouth tube is approximately halved and that in the "sample induction port" (artificial oropharynx) is reduced from about 50% to 20%. The formulation according to the invention thus makes it possible to formulate the metered-dose aerosol more advantageously with respect to a number of aspects, as the respirable dose can be virtually doubled and the undesired oropharyngeal in-vitro deposition in the sample induction port can be reduced, as can be shown by the example of beclomethasone dipropionate, budesonide and disodium cromoglycate. It is therefore to be expected that in the case of budesonide the same therapeutic effect as, for example, with the commercial product Pulmicort® is presumably achieved using half the dosage.

The invention is illustrated further by the following examples. The homogenization of active compound suspensions was in each case carried out using a rotor-stator homogenizer (Kinematika).

EXAMPLE 1

100 g of micronized disodium cromoglycate are weighed into a pressure addition vessel. After sealing and evacuating the addition vessel, 8.5 kg of HFA 227, which have previously been treated with 3% by weight of ethanol and aerated with dinitrogen oxide and adjusted to a pressure of 5 bar (20° C.) in another pressure addition vessel, are added with stirring. After homogenizing, the suspension obtained is dispensed by means of the pressure-filling technique into aluminum containers sealed with metered-dose valves.

EXAMPLE 2

2 g of micronized ipratropium bromide are weighed into a pressure addition vessel. After sealing and evacuation thereof, 6.0 kg of a mixture of HFA 227 and HFA 134a (weight ratio 80:20), which have previously been aerated with dinitrogen oxide and adjusted to a pressure of 5.5 bar at 20° C. in another pressure addition vessel, are added. After homogenizing this mixture, the suspension obtained is dispensed by means of the pressure-filling technique into containers which are equipped with a metered-dose valve.

EXAMPLE 3

5 g of micronized glycopyrronium bromide are weighed into a pressure addition vessel. After sealing and evacuation thereof, 10 kg of HFA 227, which have previously been treated with 1% by weight of ethanol and aerated with dinitrogen oxide and adjusted to a pressure of 5.25 bar (20° C.) in another pressure addition vessel, are added. After homogenizing this mixture, the suspension obtained is dispensed by means of the pressure-filling technique into pressure-resistant glass containers sealed with metered-dose valves.

EXAMPLE 4

0.6 g of micronized formoterol fumarate and 20 g of micronized glycopyrronium bromide are weighed into a pressure addition vessel. After sealing and evacuating the addition vessel, 6.5 kg of a propellant mixture of HFA 227 and HFA 134a (weight ratio 70:30), which have previously been treated with 2% by weight of ethanol and aerated with dinitrogen oxide and adjusted to a pressure of 5.5 bar (20° C.), are added with stirring. After homogenizing, the suspension obtained is dispensed by means of the pressure-filling technique into aluminum containers sealed with metered-dose valves.

EXAMPLE 5

120 g of beclomethasone dipropionate are weighed into an addition vessel and dissolved in 6 kg of ethanol in which 10 g of oleic acid have previously been dissolved. 1 g of this solution in each case is dispensed into aluminum containers and these are subsequently sealed with metered-dose valves. In a pressure addition vessel, HFA 227 is aerated with dinitrogen oxide and adjusted to a pressure of 5.5 bar at 20° C. 11 g of this mixture per container are in each case fed in under pressure and the latter is then treated in an ultrasonic bath.

EXAMPLE 6

10 g of micronized levalbuterol sulphate are weighed into a pressure addition vessel. After sealing and evacuation thereof, 13 kg of HFA 227, which have previously been treated with 650 g of ethanol and aerated with dinitrogen oxide and adjusted to a pressure of 5.25 bar (20° C.), are added. After homogenizing this mixture, the suspension obtained is dispensed into pressure-resistant containers which are equipped with metered-dose valves.

EXAMPLE 7

120 g of fluticasone are weighed into an addition vessel and dissolved in 6 kg of ethanol in which 6 g of oleic acid have previously been dissolved. 1.2 g of this solution in each case are dispensed into pressure-resistant containers and these are subsequently sealed with metered-dose valves. In a pressure addition vessel, HFA 134a is aerated with dinitrogen oxide and adjusted to a pressure of 5.5 bar at 20° C. 12 g of this mixture in each case are fed in under pressure per container and these are then treated in an ultrasonic bath.

EXAMPLE 8

3.0 g of micronized budesonide are weighed into a pressure addition vessel. After sealing and evacuation thereof, a mixture of 0.85 kg of HFA 134a and 0.85 kg of HFA 227, which have previously been aerated with dinitrogen oxide and adjusted to a pressure of 5.5 bar (20° C.) in another pressure addition vessel, is added. After homogenizing this mixture, the suspension obtained is dispensed by means of the pressure-filling technique into aluminum containers sealed with metered-dose valves.

EXAMPLE 9

3.0 g of micronized fluticasone propionate and 0.15 g of micronized formoterol fumarate are weighed into a pressure addition vessel. After sealing and evacuation thereof, a mixture of 0.5 kg of HFA 134a and 1.5 kg of HFA 227, which have previously been treated with 2% by weight of ethanol and aerated with dinitrogen oxide and adjusted to a pressure of 5.5 bar (20° C.), is added. After homogenizing this mixture, the suspension obtained is dispensed into pressure-resistant containers which are sealed with metered-dose valves.

EXAMPLE 10

5 g of micronized salmeterol xinafoate and 2 g of micronized glycopyrronium bromide are weighed into a pressure addition vessel. After sealing and evacuating the addition vessel, 70 kg of HFA 227, which have previously been treated with 2% by weight of ethanol and aerated with dinitrogen oxide and adjusted to a pressure of 5.5 bar (20° C.), are added with stirring. After homogenizing, the suspension obtained is dispensed by means of the pressure-filling technique into aluminum containers sealed with metered-dose valves.

EXAMPLE 11

10 g of sildenafil and 0.1 g of δ-tocopherol are weighed into an addition vessel and dissolved in 100 g of ethanol in which 0.1 g of lecithin has previously been dissolved. 1 g of this solution in each case is dispensed into pressure-resistant containers and these are subsequently sealed with metered-dose valves. In a pressure addition vessel, HFA 134a is aerated with dinitrogen oxide and adjusted to a pressure of 6.5 bar at 20° C. 7 g of this mixture in each case are fed in under pressure per container, which are then treated in an ultrasonic bath.

EXAMPLE 12

120 g of beclomethasone dipropionate are weighed into an addition vessel and dissolved in 6 kg of ethanol in which 120 g of glycerol have previously been dissolved. 1 g of this solution in each case is dispensed into aluminum containers and these are subsequently sealed with metered-dose valves. In a pressure-addition vessel, HFA 227 is aerated with dinitrogen oxide and adjusted to a pressure of 5.5 bar at 20° C. 11 g of this mixture in each case are fed in under pressure per container and these are then treated in an ultrasonic bath.

EXAMPLE 13

10 g of sildenafil and 0.1 g of δ-tocopherol are weighed into an addition vessel and dissolved in 100 g of ethanol in which 1 g of glycerol has previously been dissolved. 1 g of this solution in each case is dispensed into pressure-resistant containers and these are subsequently sealed with metered-dose valves. In a pressure addition vessel, HFA 227 is aerated with dinitrogen oxide and adjusted to a pressure of 6 bar at 20° C. 6 g of this mixture in each case are fed in under pressure per container, which are then treated in an ultrasonic bath.

EXAMPLE 14

1.6 g of micronized budesonide are weighed into a pressure addition vessel. After sealing and evacuation thereof, a mixture of 20 g of propylene glycol, 30 g of ethanol and 950 g of HFA 227, which have previously been aerated with dinitrogen oxide and adjusted to a pressure of 5.5 bar (20° C.) in another pressure addition vessel, is added. After homogenizing this mixture, the suspension obtained is dispensed by means of the pressure-filling technique into aluminum containers sealed with metered-dose valves.

EXAMPLE 15

1.6 g of micronized budesonide are weighed into a pressure addition vessel. After sealing and evacuation thereof, a mixture of 50 g of glycerol, 150 g of ethanol and 800 g of HFA 134a, which has previously been aerated with dinitrogen oxide and adjusted to a pressure of 6.5 bar (20° C.) in another pressure addition vessel, is added. After homogenizing this mixture, the solution obtained is dispensed by means of the pressure-filling technique into aluminum containers sealed with metered-dose valves.

What is claimed is:

1. A pressure-liquefied propellant mixture for aerosols, comprising dinitrogen monoxide and a hydrofluoroalkane of formula $$C_xH_yF_z \qquad (I)$$

in which x is the number 1, 2 or 3, y and z are each an integer $\geq 1$ and y+z=2x+2.

2. The propellant mixture as claimed in claim 1, comprising at least 40% by weight of the hydrofluoroalkane of the formula I, based on the total weight of the mixture.

3. The propellant mixture as claimed in claim 1, comprising at least 64% by weight of the hydrofluoroalkane of the formula I, based on the total weight of the mixture.

4. The propellant mixture as claimed in claim 1, wherein the hydrofluoroalkane of the formula I is selected from the group consisting of 1,1,1,2,-tetrafluoroethane, 1,1,1,2,3,3,3-heptafluoropropane and 1,1,1,2,-tetrafluoroethane in the presence of 1,1,1,2,3,3,3-heptafluoropropane.

5. The propellant mixture as claimed in claim 1, having at 20° C. a pressure ranging from 3 to 10 bar.

6. The propellant mixture as claimed in claim 1, further comprising carbon dioxide.

7. The propellant mixture as claimed in claim 1, comprising at least 0.0001% by weight of dinitrogen monoxide, based on the total weight of the mixture.

8. The propellant mixture as claimed in claim 1, comprising 0.0001% to 10% by weight of dinitrogen monoxide, based on the total weight of the mixture.

9. The propellant mixture as claimed in claim 1, further comprising a cosolvent in an amount of from 0.01% to 40% by weight, based on the total weight of the mixture.

10. The propellant mixture as claimed in claim 9, wherein the cosolvent is selected from the group consisting of water, ethanol, propanol, ethylene glycol, propylene glycol, glycerol, propane, butane, isobutane, pentane, dimethyl ether and diethyl ether.

11. A medicinal aerosol formulation, comprising an efficacious amount of a pharmaceutically active compound and a pressure-liquefied propellant mixture, comprising dinitrogen monoxide and a hydrofluoroalkane of formula $$C_xH_yF_z \qquad (I)$$

in which x is the number 1, 2 or 3, y and z are each an integer $\geq 1$ and y+z=2x+2.

12. The aerosol formulation as claimed in claim 11, comprising at least 30% by weight of the hydrofluoroalkane of the formula I, based on the total weight of the formulation.

13. The aerosol formulation as claimed in claim 11, comprising at least 64% by weight of the hydrofluoroalkane of the formula I, based on the total weight of the formulation.

14. The aerosol formulation as claimed in claim 11, wherein the hydrofluoroalkane of the formula I is selected from the group consisting of 1,1,1,2-tetrafluoroethane, 1,1,1,2,3,3,3-heptafluoropropane and 1,1,1,2-tetrafluoroethane in the presence of 1,1,1,2,3,3,3-heptafluoropropane.

15. The aerosol formulation as claimed in claim 11, having at 20° C. a pressure ranging from 3 to 10 bar.

16. The aerosol formulation as claimed in claim 11, further comprising carbon dioxide.

17. The aerosol formulation as claimed in claim 11, comprising at least 0.0001% by weight of dinitrogen monoxide, based on the total weight of the formulation.

18. The aerosol formulation as claimed in claim 11, comprising 0.0001% to 10% by weight of dinitrogen monoxide, based on the total weight of the formulation.

19. The aerosol formulation as claimed in claim 11, comprising a cosolvent in an amount of from 0.01% to 40% by weight, based on the total weight of the formulation.

20. The aerosol formulation as claimed in claim 19, wherein the cosolvent is selected from the group consisting of water, ethanol, propanol, ethylene glycol, propylene glycol, glycerol, propane, butane, isobutane, pentane, dimethyl ether and diethyl ether.

21. The aerosol formulation as claimed in claim 11, further comprising a surface-active agent.

22. The aerosol formulation as claimed in claim 11, further comprising 0.0001% to 1% by weight of surface-active agent, based on the total weight of the formulation.

23. The aerosol formulation as claimed in claim 11, being essentially free of surface-active agents.

24. The aerosol formulation as claimed in claim 11, wherein the pharmaceutically active compound is selected from the group consisting of salbutamol, formoterol, salmeterol, fluticasone, budesonide, ciclesonide, glycopyrronium, tiotropium, cromoglycic acid, nedocromil, mometasone, sildenafil, beclomethasone, levalbuterol and pharmaceutically acceptable salts and derivatives thereof.

25. A process for the preparation of a medicinal aerosol formulation, comprising an efficacious amount of a pharmaceutically active compound and a pressure-liquefied propellant mixture, comprising dinitrogen monoxide and a hydrofluoroalkane of formula $$C_xH_yF_z \qquad (I)$$

in which x is the number 1, 2 or 3, y and z are each an integer $\geq 1$ and y+z=2x+2, said process comprising the steps of introducing dinitrogen monoxide under pressure into the liquefied hydrofluoroalkane and adding the pharmaceutically active compound.

26. The propellant mixture as claimed in claim 1, comprising at least 87%. by weight of the hydrofluoroalkane of the formula I, based on the total weight of the mixture.

27. The propellant mixture as claimed in claim 1, having at 20° C. a pressure ranging from 3.5 to 6 bar.

28. The propellant mixture as claimed in claim 1, comprising at least 0.01% by weight of dinitrogen monoxide, based on the total weight of the mixture.

29. The propellant mixture as claimed in claim 1, comprising 0.01% to 6% by weight of dinitrogen monoxide, based on the total weight of the mixture.

30. The propellant mixture as claimed in claim 1, comprising 0.01% to 2% by weight of dinitrogen monoxide, based on the total weight of the mixture.

31. The propellant mixture as claimed in claim 1, further comprising carbon dioxide and having a total content of dinitrogen and carbon dioxide of from 0.01% to 6% by weight, based on the total weight of the mixture.

32. The propellant mixture as claimed in claim 1, further comprising carbon dioxide and having a total content of dinitrogen monoxide and carbon dioxide of from 0.01% to 6% by weight, based on the total weight of the mixture.

33. The propellant mixture as claimed in claim 1, further comprising carbon dioxide and having a total content of dinitrogen monoxide and carbon dioxide of from 0.01% to 2% by weight, based on the total weight of the mixture.

34. The propellant mixture as claimed in claim 1, further comprising a cosolvent in an amount of from 0.1% to 15% by weight, based on the total weight-of the mixture.

35. The aerosol formulation as claimed in claim 11, comprising at least 40% by weight of the hydrofluoroalkane of the formula I, based on the total weight of the formulation.

36. The aerosol formulation as claimed in claim 11, comprising at least 87% by weight of the hydrofluoroalkane of the formula I, based on the total weight of the formulation.

37. The aerosol formulation as claimed in claim 11, having at 20° C. a pressure ranging from 3.5 to 6 bar.

38. The aerosol formulation as claimed in claim 11, comprising at least 0.01% by weight of dinitrogen monoxide, based on the total weight of the formulation.

39. The aerosol formulation as claimed in claim 11, comprising 0.01% to 6% by weight of dinitrogen monoxide, based on the total weight of the formulation.

40. The aerosol formulation as claimed in claim 11, comprising 0.01% to 2% by weight of dinitrogen monoxide, based on the total weight of the formulation.

41. The aerosol formulation as claimed in claim 11, further comprising carbon dioxide and having a total content of dinitrogen and carbon dioxide of from 0.0001% to 10% by weight, based on the total weight of the formulation.

42. The aerosol formulation as claimed in claim 11, further comprising carbon dioxide and having a total content of dinitrogen and carbon dioxide of from 0.01% to 6% by weight, based on the total weight of the formulation.

43. The aerosol formulation as claimed in claim 11, further comprising carbon dioxide and having a total content of dinitrogen and carbon dioxide of from 0.01% to 2% by weight, based on the total weight of the formulation.

44. The aerosol formulation as claimed in claim 11, further comprising a cosolvent in an amount of from 0.1% to 15% by weight, based on the total weight of the formulation.

45. The aerosol formulation as claimed in claim 21, wherein the surface-active agent is selected from the group consisting of oleic acid, lecithin, sorbitan trioleate, cetylpyridinium chloride, benzalkonium chloride, polyoxyethylene (20) sorbitan monolaurate, polyoxyethylene (10) stearyl ether, polyoxyethylene (2) oleyl ether, polyoxyethylene (20) sorbitan monostearate, polyoxyethylene (20) sorbitan monooleate, a polyoxypropylene/polyoxyethylene block copolymer, a polyoxypropylene/polyoxyethylene/ ethylenediamine block copolymer and ethoxylated castor oil.

46. The aerosol formulation as claimed in claim 11, further comprising 0.001% to 0.1% by weight of the surface-active agent, based on the total weight of the formulation.

47. An inhalable medicinal aerosol formulation, administrable by a metered dose inhaler, comprising an effective amount of a pharmaceutically active compound and a pressure-liquefied homogeneous propellant mixture comprising dinitrogen monoxide and a hydrofluoroalkane of formula

$$C_xH_yF_z \quad \quad (I)$$

in which x is the number 1, 2 or 3, y and z are each an integer $\geq 1$ and y+z=2x+2,
the dinitrogen monoxide being present in an amount of from 0.01% to 2% by weight, based on the total weight of the formulation.

48. The aerosol formulation as claimed in claim 47, comprising at least 64% by weight of the hydrofluoroalkane of the formula I, based on the total weight of the formulation.

49. The aerosol formulation as claimed in claim 47 or 48, wherein the hydrofluoroalkane of the formula I is selected from the group consisting of 1,1,1,2-tetrafluoroethane, 1,1,1,2,3,3,3-heptafluoropropane and 1,1,1,2,-tetrafluoroethane in the presence of 1,1,1,2,3,3,3-heptafluoropropane.

50. The aerosol formulation as claimed in claim 47 or 48, wherein the pharmaceutically active compound is selected from the group consisting of salbutamol, formoterol, salmeterol, fluticasone, budesonide, ciclesonide, glycopyrronium, tiotropium, cromoglycic acid, nedocromil, mometasone, 'sildenafil, beclomethasone, levalbuterol, and pharmaceutically acceptable salts and derivatives thereof.

51. An inhalable medicinal aerosol formulation administrable by a metered dose inhaler, comprising an effective amount of a pharmaceutically active compound selectd from the group consisting of salbutamol, formoterol, salmeterol, fluticasone, dudesonide, ciclesonide, glycopyrronium, tiotropium, cromoglycic acid, nedocromil, mometasone, sildenafil, becomethasone, levalbuterol and pharmaceutically acceptale salts and derivatibves thereof, and a pressure-liquefied homogeneous propellant mixure comprising dinitrogen monoxide and a hydrofluoroalkane selected from the group consisting of 1,1,1,2,-tetrafluoroethane, 1,1,1,2,3,3,3-heptafluoropropane and 1,1,1,2-tetrafluoroethane in the presence of 1,1,1,2,3,3,3-heptafluoropropane, the dinitrogen monoxide being present in an amount of from 0.01% to 2% by weight, based on the total weight of the formulation, and the hydrofluoroalkane being present in an amount of at least 64% by weight, on the total weight of the formulation.

* * * * *